United States Patent [19]

Wright et al.

[11] 4,044,148

[45] Aug. 23, 1977

[54] COMPOUNDS, COMPOSITIONS AND METHODS OF USE

[75] Inventors: John B. Wright; Charles M. Hall, both of Kalamazoo, Mich.

[73] Assignee: The Upjohn Company, Kalamazoo, Mich.

[21] Appl. No.: 651,480

[22] Filed: Jan. 22, 1976

Related U.S. Application Data

[63] Continuation of Ser. No. 477,818, June 10, 1974, abandoned, which is a continuation-in-part of Ser. No. 382,762, July 26, 1973, Pat. No. 3,993,679, which is a continuation-in-part of Ser. No. 317,005, Dec. 20, 1972, abandoned.

[51] Int. Cl.² .................... A01N 9/24; C07C 101/447
[52] U.S. Cl. ................................................. 424/317
[58] Field of Search .......... 260/501.1, 501.15, 501.17, 260/518 R, 518 A, 519; 424/315, 317

[56] References Cited

U.S. PATENT DOCUMENTS 3,966,965  6/1976  Sellstedt et al. ................ 424/226 X

*Primary Examiner*—Anton H. Sutto
*Attorney, Agent, or Firm*—Martin B. Barancik; Roman Saliwanchik

[57] ABSTRACT

It has now been discovered that novel compounds of Formula 1

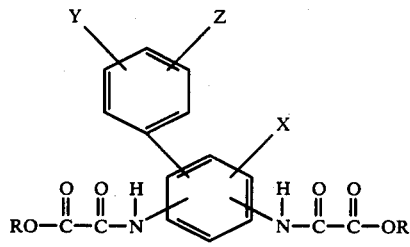

are useful in the prophylactic treatment of sensitized humans and animals for allergy and all anaphylactic reactions of a reagin or non-reagin mediated nature. Additionally, the compounds are formulated with pharmaceutical carriers for oral, parenteral, inhalation, or rectal means of administration.

23 Claims, No Drawings

COMPOUNDS, COMPOSITIONS AND METHODS OF USE

CROSS REFERENCE TO RELATED APPLICATIONS

This is a continuation of pending application Ser. No. 477,818 filed June 10, 1974, now abandoned, which is a continuation-in-part of copending U.S. application Ser. No. 382,762 filed July 26, 1973, now U.S. Pat. No. 3,993,679 which is a continuation-in-part of copending U.S. application Ser. No. 317,005 filed Dec. 20, 1972, and now abandoned.

BRIEF SUMMARY OF THE INVENTION

It has now been discovered that novel compounds of Formula 1 are useful in the prophylactic treatment of sensitized humans and animals for allergy and all anaphylactic reactions of a reagin or non-reagin mediated nature. Additionally, the compounds are formulated with pharmaceutical carriers for oral, parenteral, inhalation, or rectal means of administration.

DETAILED DESCRIPTION OF THE INVENTION

In accordance with invention, compounds of Formula 1, hereafter referred to as Group A, are provided

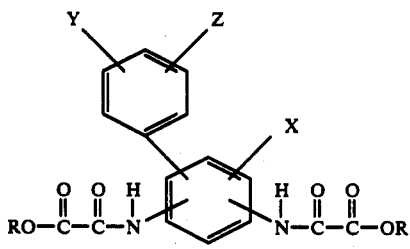

wherein the

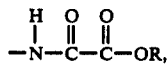

groups are meta or para to each other; R is hydrogen or a physiologically acceptable metal or amine cation; X, Y, and Z are the same or different and are selected from the group consisting of hydrogen, alkyl of one to six carbon atoms, inclusive, alkoxy of one to four carbon atoms, inclusive, hydroxy, fluoro, chloro, bromo and

wherein D is selected from the group consisting of hydrogen, alkyl of one to six carbon atoms, inclusive, and a physiologically acceptable metal or amine cation; with the proviso that when D is hydrogen or a physiologically acceptable metal or amine cation, D is the same as R.

Another group of compounds hereafter known as Group B are those compounds of Group A wherein Y is hydrogen.

A further group of compounds are those compounds of Group B wherein Z is hydrogen, A still further group of compounds, hereafter known as Group D, are those compounds of Group A wherein when one or all of X, Y, Z and D is alkyl, alkyl has a maximum limitation of three carbon atoms and when one or all of X, Y, and Z is alkoxy, then alkoxy has a maximum number of three carbon atoms.

A further group of compounds, hereafter known as Group E, are those compounds where X, Y and Z are the same or different and are selected from the group consisting of hydrogen, alkyl of one to three carbon atoms, inclusive, alkoxy of one to three carbon atoms, inclusive, fluoro, chloro, and

wherein D is selected from the group consisting of hydrogen, alkyl of one to three carbon atoms, inclusive, and a physiologically acceptable metal or amine cation, with the proviso that when D is hydrogen or a physiologically acceptable metal or amine cation, D is the same as R. The position of the

groups and R are defined as in Group A.

A still further group of compounds, hereafter known as Group F, are compounds of Group E wherein the

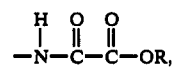

groups are meta to each other.

A further group of compounds, hereafter referred to as Group G, are compounds of Group F wherein the phenyl ring is meta to both the

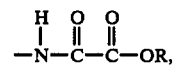

groups.

A still further group of compounds, hereafter referred to as Group H, are compounds of Group G wherein X is ortho to both

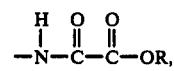

groups.

Another group of compounds, hereafter referred to as Group I, are compounds of Group H wherein Y is hydrogen.

A still further group of compounds are compounds of Group I wherein Z is hydrogen.

The preferred compound is N,N'(2-chloro-5-phenyl-m-phenylene)dioxamic acid.

As used in the above disclosure and throughout the specification the phrase "alkyl of one to six carbon atoms, inclusive" includes methyl, ethyl, propyl, butyl, pentyl, hexyl and isomers thereof. Illustrative examples of isomers include isopropyl, tert. butyl, neopentyl and 2,2-dimethylbutyl. Limitations of different carbon number are interpreted in the same manner.

The phrase "a physiologically acceptable metal or amine cation" is that metal or amine which is accepted in an essentially non-toxic manner by a mammel. Illustrative examples of such metals are the alkali metals, e.g., lithium, sodium and potassium, and the alkaline earth metals, e.g., magnesium and calcium. Other metals, e.g., aluminum, zinc, and iron are also within the scope of this invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about eighteen carbon atoms, as well as heterocyclic amines, e.g., piperidine, morpholine, pyrrolidine, piperazine, and lower-alkyl derivatives thereof, e.g., 1-methyl piperidine, 4-ethylmorpholine, 1-isoproplpyrrolidine, 2-methylpyrrolidine, 1,4-dimethylpiperazine, 2-methylpiperidine, 1,5-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-metjyl-1-propanol, tris(hydroxymethyl)aminomethane (THAM), N-phenylethanolamine, N-(p-tert amylphenyl)diethanolamine, glactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium and the like.

The compounds of the invention can be prepared by methods known in the art. For example, methods outlined in U.S. Pat. No. 3,639,249, Column 3, line 38, to Column 5, line 18, can be used with facility to form the ester. From thereon, the ester is readily converted to metal salts, the free acid, or amine salts by conventional methods. The disclosure of U.S. Ser. No. 382,762 at Page 8, line 4, to Page 9, line 4, and Page 10, line 2, to Page 11, line 23, also discloses methods of preparing the compounds of this invention. The above disclosures are incorporated by reference into this application.

Following is an illustrative list of compounds of the invention which can be prepared by the above disclosed procedures:

TABLE I

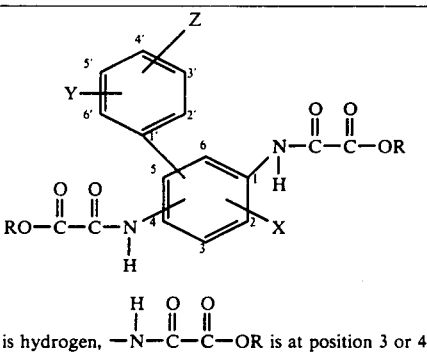

R is hydrogen, —N—C—C—OR is at position 3 or 4

| X | Y | Z | $\begin{array}{c}Y\\ \phantom{x}\\ \phantom{x}\text{-Z}\end{array}$ |
|---|---|---|---|
| H | H | H | 5 |
| 2—Cl | H | H | 5 |
| 6—Cl | H | H | 5 |
| 2—F | H | H | 5 |
| 2—CH₃ | H | H | 5 |
| 2—i—C₃H₇ | H | H | 5 |
| 2—C₅H₁₁ | H | H | 5 |
| 2—i—C₆H₁₃ | H | H | 5 |
| 2—OH | H | H | 5 |
| 2—OCH₃ | H | H | 5 |
| 2—OC₃H₇ | H | H | 5 |
| 2—OC₆H₁₃ | H | H | 5 |
| 2—Br | H | H | 5 |
| 2—CCOH | H | H | 5 |
| 2—COOC₄H₃ | H | H | 5 |
| 6—i—C₃H₇ | H | H | 5 |
| 6—OH | H | H | 5 |
| 6—OC₃H₇ | H | H | 5 |
| 6—COOC₂H₅ | H | H | 5 |
| 2—Cl | 2'—Cl | 6'—Cl | 5 |
| 2—C₂H₅ | 3'—OCH₃ | 5'—COC₅H₁₁ | 5 |
| 2—OC₄H₃ | 4'—C₂H₅ | 5—Cl | 5 |
| 2—F | 4'—COCH₃ | H | 5 |
| 5—Br | H | H | 2 |
| 5—CH₃ | 2'—CH₃ | 5'—CH₃ | 2 |
| 5—OC₃H₇ | 3'—COOH | 5'—C₂H₅ | 2 |
| 5—COOC₂H₅ | —4'—Cl | H | 2 |
| 6—Cl | 3'—OCH₃ | H | 2 |
| 6—C₄H₃ | 2'—Cl | 4'—COOCH₃ | 2 |
| 6—OCH₃ | 2'—OCH₃ | 6'—OCH₃ | 2 |
| 6—COOC₃H₇ | H | H | 2 |
| 5—Cl | H | H | 6 |
| 5—I—C₅H₁₃ | H | 4'—Cl | 6 |
| 5—OCH₃ | 2'—COOCH₃ | 4'—Br | 6 |
| 5—COOC₂H₅ | 3'—OC₂H₅ | 6 |  |

TABLE II

The compounds of Table I are converted to their physiologically acceptable metal or amine cations by standard means.

The following examples are compounds in accordance with the invention. They are not intended to limit but merely to exemplify the invention.

EXAMPLE 1

N,N'-(2-Chloro-5-phenyl-m-phenylene)dioxamic acid a. 2-Chloro-5-phenyl-m-phenylenediamine A solution of 2.79 g. (0.01 mole) of 4-chloro-3,5-dinitrobiphenyl [R. C. Hall and C. S. Giam, J. Agr. Food Chem 20 (3) 546–52 (1972)] in 200 ml. of dioxane is hydrogenated at 3 atmospheres using Raney Nickel Catalyst. The catalyst is removed by filtration and the residue concentrated under reduced pressure. The residue is recrystallized from ethanol-water. There is obtained 1.12 g. (51%) of material melting point at 142°–144.5°. Additional recrystallization raises the melting point to 146.7°.

Anal. Calcd. for: $C_{12}H_{11}ClN_2$: C, 65.91; H, 5.07; Cl, 16.21; N, 12.81. Found: C, 65.75; H, 5.26; Cl, 15.52; N, 12.76.

b. Diethyl N,N'-(2-chloro-5-phenyl-m-phenylene)dioxamate

To a stirred solution of 7.45 g (0.034 mole) of 2-chloro-5-phenyl-m-phenylene diamine in 16 ml. of dry ethyl acetate and 8.30 g (0.082 mole) of triethylamine, cooled below 5° is added, dropwise, 11.20 g. (0.082 mole) of ethyl oxalyl chloride. An additional 20 ml. of ethyl acetate is added, the mixture is stirred in the ice-bath for an additional hour and then overnight at room temperature.

The mixture is diluted to a volume of 200 ml. by the addition of ethyl acetate and the solid removed by filtration and washed with water. The ethyl acetate filtrate is concentrated to dryness to give additional material.

The solids are combined and recrystallized from ethanol. There is obtained 11.66 g. (78%) of long thin rose-colored needles melting at 204°– 205°.

Anal. Calcd. for: $C_{20}H_{19}ClN_2O_6$: C, 57.36; H, 4.57; Cl, 8.46; N, 6.96. Found: C, 57.38; H, 4.52; Cl, 8.51; N, 6.73.

c. N,N'-(2-Chloro-5-pyhenyl-m-phenylene)dioxamic acid

A solution of 5.00 g (0.12 mole) of diethyl-N,N'-(2-chloro-5-phenyl-m-phenylene)dioxamate in 125 ml. of chloroform is mixed in a separation funnel with 29 ml. of 1 M NaOH. Water (approximately 900 ml.) if added to dissolve all the solids. The aqueous phase is drawn off through a filter into a flask. After stirring for fifteen minutes, 30 ml. of 1 M CHI is added. The precipitate which forms is collected by filtration. The solid obtained is recrystallized from $H_2O$ to give 2.41 g. (55%) of product, M.P. 190° (dec.). A second recrystallization raises the melting point to 195° (dec.).

EXAMPLE 2

N,N'-(4-Chloro-5-phenyl-m-pyhenylene)dioxamic acid a. 3,5-Dinitro-2-biphenylol

The procedure of Borche and Scholtin [Chem. Ber. 50, 602] is followed.

To a stirred solution of 25 g. (0.15 mole) of 2-phenylphenol in 250 ml. of glacial acetic acid at 30° is added a solution of 25 ml. of nitric acid in 75 ml. of glacial acetic acid. The temperature is kept below 40°. The mixture is heated on a steam bath for 30 minutes. The mixture is cooled to room temperature and poured into 300 g. of ice. The precipitate is removed by filtration and washed with water and ethanol. There is obtained 31.4 g. (81%) of yellow crystalline material melting at 204°-205°.

b. 2-Chloro-3,5-dinitrobiphenyl

A mixture of 30.00 g. of 3,5-dinitro-2-biphenylol, 15 ml. of dimethylformamide, and 113 ml. of phosphorous oxychloride is heated on a steam bath for 2.25 hours. The mixture is then cooled to room temperature and poured slowly into approximately 600 g. of crushed ice. The precipitate that forms is isolated by filtration and washed with water. The solid is dissolved in chloroform and the chloroform solution is washed several times with 10% $Na_2CO_3$ and once with water. The chloroform solution is dried over $MgSO_4$ and concentrated. The product is recrystallized from benzenehexane to give 19.07 g. of material (melting at 119°–20° ).

c. 4-Chloro-5-phenyl-m-phenylene diamine

A solution of 10.00 g. (0.0359 mole) of 2-chloro-3,5-dinitrobiphenyl in 200 ml. of dioxane is hydrogenated at 3 atmospheres of hydrogen using Raney nickel Catalyst. The catalyst is removed by filtration and the filtrate is concentrated under reduced pressure. 110 ml. of benzene is added to the residue and this is removed by distillation. The resulting oil is used directly in the following reaction.

d. Diethyl N,N'-(4-Chloro-5-phenyl-m-phenylene)dioxamate

To a solution 7.89 g. (0.036 mole) of 4-chloro-5-phenyl-m-phenylene diamine in 8.80 g. (0.087 mole) of triethylamine and 20 ml. of ethyl acetate cooled in an ice bath to 5° is added 11.90 g. (0.087 mole) of ethyl oxalyl chloride, keeping the temperature below 15°. The reaction mixture is allowed to stand overnight at room temperature. To the reaction mixture is added 200 ml. of chloroform and the mixture is filtered. The precipitate is added to water and this is filtered. The water insoluble material is dissolved in chloroform and the solution is added to the original filtrate. The resulting solution is concentrated and the residue is recrystallized from ethanol with charcoal treatment. There is obtained 12.25 g. (83%) of material melting at 184.2°–85.2°.

Anal. Calcd. for: $C_{20}H_{19}ClN_2O_6$ C, 57.36, H, 4.57; Cl, 8.46; N, 6.99. Found: C, 57,36; H, 4,58; Cl, 8.39; N, 6.62.

e. N,N'-(4-Chloro-5-phenyl-m-phenylene)dioxamic acid

To a solution of 5.0 g (0.014 mole) of diethyl N,N'-(4-Chloro-5-phenyl-m-phenylene)dioxamate in 125 ml. of chloroform in a separatory funnel is added 29 ml. of 1 M sodium hydroxide solution. Water is added to the mixture until the solid that forms on shaking redissolves. The mixture is allowed to stand with occasional shaking for fifteen minutes. The aqueous layer is drawn off, filtered and the filtrate acidified by the addition of 1N hydrochloric acid. The precipitate that forms is removed by filtration. There is obtained 3.89 g. of material melting above 310°.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acecia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal supporitories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3)an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while ihhaling.

Aerosols are prepared by dispersing a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodiflurormethane (Freon 12), dichlorotetrafluoroethane (Freon 114), trichloromonofluoromethane (Freon 11), dichloromonofluoromethane (Freon 21), monochlorodifluoromethane (Freon 22), trichlorotrifluoroethane (Freon 113), difluoroethane (Genetron 142-A) and monochlorotrifluoromethane (Freon 13).

The term "unit dosage form," as used in the specification and claims, refers to physically discrete units suitable as unitary dosages for human subjects and animals, each unit containing a predetermined quantity of active material calculated to produce the desired therapeutic effect in associated with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.01 to about 20 mg. of compound in a single dose, administered parenterally or by inhalation in the compositions of this invention, are effective for preventing allergy attacks. More specifically, the single dose is from about 0.5 to about 10 mg. of compound. The oral and rectal dose is from about 5.0 to about 250 mg. in a single dose. More specifically, the single dose is from about 10 to about 125 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 3

A lot of 10,000 tablets, each containing 50 mg. of N,N'-(2-Chloro-5-phenyl-m-phenylene)dioxamic acid is prepared from the following types and amounts of ingredients:

| | |
|---|---|
| N,N'-2(Chloro-5-phenyl-m-phenylene-dioxamic acid | 500 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every 6 hours.

EXAMPLE 4

One thousand tablets, each containing 100 mg. of N,N'-(2-Chloro-5-phenyl-m-phenylene)dioxamic acid are prepared from the following types and amounts of ingredients:

| | |
|---|---|
| N,N'-(2-Chloro-5-phenyl-m-phenylene)-dioxamic acid | 100 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before means.

EXAMPLE 5

A sterile preparation suitable for intramuscular injection and containing 4.0 mg. of N,N'-(2-Chloro-5-phenylene)dioxamic acid in each milliliter is prepared from the following ingredients:

| | |
|---|---|
| N,N'-(2-Chloro-5-phenyl-m-phenylene)-dioxamic acid | 4.0 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 6

Six hundred ml. of an aqueous suspension containing 20 mg. of the N,N'-(2-Chloro-5-phenyl-m-phenylene)dioxamic acid per ml. is prepared as follows:

| | |
|---|---|
| N,N'-(2-Chloro-5-phenyl-m-phenylene)-dioxamic acid | 12 Gm. |
| Sodium chloride | 5 Gm. |
| Water for injection q.s. | 600 ml. |

The N,N'-(2-Chloro-5-m-phenylene)-dioxamicacid and sodium chloride are dispersed in sufficient water to make 600 ml. and sterilized.

The liquid is placed in nebulizers designed to deliver 0.25 ml. per spray.

The liquid is inhaled into the lungs every 4 to 6 hours for prevention of asthmatic attacks.

EXAMPLE 7

A powder mixture consisting of 1.0 gram of N,N'-(2-Chloro-5-phenyl-m-phenylene)dioxamic acid and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 8

A powder mixture consisting of 2.0 gram of N,N'-(2-Chloro-5-phenyl-m-phenylene)dioxamic acid and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every four hours for prevention of rhinitis.

EXAMPLE 9

Twelve grams of an aerosol composition are prepared from the following ingredients:

| | |
|---|---|
| N,N'-(2-Chloro-5-phenyl-m-phenylene)-dioxamic acid | 0.500 Gm. |
| Freon 12 | 1.440 Gm. |
| Freon 114 | 2.160 Gm. |
| Water | 7.788 Gm. |
| Sorbitan monoleate | 0.600 Gm. |

The compound is dispersed in water and chilled to −30° C. and added to the chilled Freons. The twelve grams of composition are added to a 13 ml. plastic coated bottle and capped with a metering valve. The metering valve releases 80 mg. of composition in an aerosol. The aerosol is inhaled every four to six hours for prevention of asthmatic attacks.

EXAMPLE 10

After allowing for the differeing solubilities of the compounds and the activity of the particular compound as measured, for example, by the in vivo, rat passive cutaneous anaphylaxis assay, a suitable quantity of each of the compounds of Table I through Table II and Examples 1–2, is substituted for the active compound in the compositions and uses of Examples 3 through 9. Results showing anti-allergy activity are obtained.

It should be noted that in all the compositions and treatment examples of this patent application, the quantity of drug employed refers to the acid equivalent.

When repeated administration is desired, the compounds of this application which have a relatively short duration of activity can be administered in a priming dose-maintenance dose regimen as described in U.S. Ser. No. 382,762 at Page 58, line 19, to Page 59, line 9.

Following the rat passive cutaneous anaphylaxis assay procedure of Example 3 of U.S. Ser. No. 382,762, the inhibitory dose$_{50}$ of N,N'-(2-chloro-5-phenyl-m-phenylene)dioxamic acid is 0.01 mg./kg. by the intravenous route.

We claim:

1. A pharmaceutical composition which comprises an anti-reagin or non-reagin mediated allergy effective amount of a compound

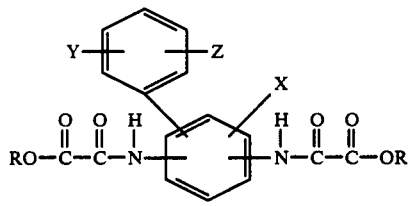

wherein the

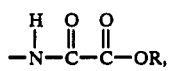

groups or meta or para to each other; R is hydrogen or a physiologically acceptable metal or amine cation; and X, Y, and Z are the same or different and are selected from the group consisting of hydrogen, alkyl of one to six carbon atoms, inclusive, alkoxy of one to four carbon atoms, inclusive, hydroxy, fluoro, chloro, bromo and

wherein D is selected from the group consisting of hydrogen, alkyl of one to six carbon atoms, inclusive, and a physiologically acceptable metal or amine cation, with the proviso that when D is hydrogen or a physiologically acceptable metal or amine cation, D is the same as R; in association with a pharmaceutical carrier.

2. Compositions in accordance with claim 1 wherein the

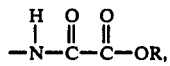

groups are meta to each other, the phenyl substituent is meta to both

groups and X is chloro which is ortho to both

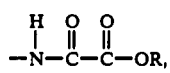

groups.

3. Compositions in accordance with claim 2 wherein R is hydrogen.

4. Compositions in accordance with claim 2 wherein R is sodium.

5. Compositions in accordance with claim 2 wherein R is tris(hydroxymethyl)ammonium.

6. Compositions in accordance with claim 1 adapted for oral or inhalation means.

7. A method for prophylactically treating allergy of a reagin or non-reagin mediated nature in a mammal which comprises administering to a mammal in need of said treatment an anti-reagin or non-reagin mediated allergy effective amount of a compound of the structure

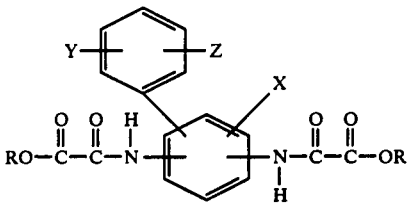

wherein the

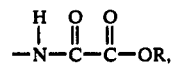

groups are meta or para to each other; R is hydrogen or a physiologically acceptable metal or amine cation; and X, Y and Z are the same or different and are selected from the group consisting of hydrogen, alkyl of one to six carbon atoms inclusive, alkoxy of one to four carbon atoms, inclusive, hydroxy, fluoro, chloro, bromo and

wherein D is selected from the group consisting of hydrogen, alkyl of one to six carbon atoms, inclusive, and a physiologically acceptable metal or amine cation, with the proviso that when D is hydrogen or a physiologically acceptable metal or amine cation, D is the same as R; in association with a pharmaceutical carrier.

8. A method in accordance with claim 7 wherein the administration is by the oral or inhalation route.

9. Compounds of the structure

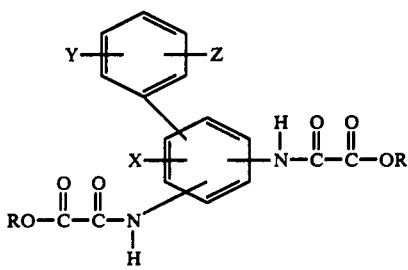

wherein the

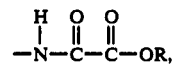

groups are meta or para to each other; R is hydrogen or a physiologically acceptable metal or amine cation; and X, Y and Z are the same or different and are selected from the group consisting of hydrogen, alkyl of one to six carbon atoms inclusive, alkoxy of one to four carbon atoms, inclusive, hydroxy, fluoro, chloro, bromo and

wherein D is selected from the group consisting of hydrogen, alkyl of one to six carbon atoms, inclusive, and a physiologically acceptable metal or amine cation, with the proviso that when D is hydrogen or a physiologically acceptable metal or amine cation, D is the same as R.

10. Compounds in accordance with claim 9 wherein Y is hydrogen.

11. Compounds in accordance with claim 10 wherein Z is hydrogen.

12. Compounds in accordance with claim 9 wherein when one or more of X, Y, Z and D is alkyl, alkyl has a maximum limitation of three carbon atoms; and when one or more of X, Y, and Z is alkoxy, alkoxy has a maximum limitation of three carbon atoms.

13. Compounds in accordance with claim 9 wherein X, Y and Z are the same or different and are selected from the group consisting of hydrogen, alkyl of one to three carbon atoms, inclusive, alkoxy of one to three carbon atoms, inclusive, fluoro, chloro and

wherein D is selected from the group consisting of hydrogen, alkyl of one to three carbon atoms, inclusive, and a physiologically acceptable metal or amine cation with the proviso that when D is hydrogen or a physiologically acceptable metal or amine cation, D is the same as R.

14. Compounds in accordance with claim 13 wherein the

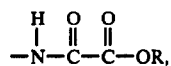

groups are meta to each other.

15. Compounds in accordance with claim 14 wherein the phenyl substituent is meta to both the

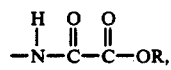

groups.

16. Compounds in accordance with claim 15 wherein X is ortho to both

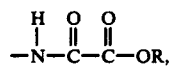

groups.

17. Compounds in accordance with claim 16 wherein Y is hydrogen.

18. Compounds in accordance with claim 17 wherein Z is hydrogen.

19. Disodio N,N'-(2-chloro-5-phenyl-m-phenylene)-dioxamate according to claim 9.

20. N,N'-(2-chloro-5-phenyl-m-phenylene)dioxamic acid according to claim 9.

21. Disodio N,N'-(4-chloro-5-phenyl-m-phenylene)-dioxamate according to claim 9.

22. N,N'-(4-chloro-5-phenyl-m-phenylene)dioxamic acid according to claim 9.

23. Ditris(hydroxymethyl)methylammonium N,N'-(2-chloro-5-phenyl-m-phenylene)dioxamate according to claim 9.

* * * * *

UNITED STATES PATENT OFFICE
CERTIFICATE OF CORRECTION

Patent No. 4,044,148  Dated 23 August 1977

Inventor(s) John B. Wright, et al

It is certified that error appears in the above-identified patent and that said Letters Patent are hereby corrected as shown below:

Column 2, line 68, "mammel" should read -- mammal --;
Column 4, line 30, "2-COOC$_4$H$_3$" should read -- 2-COOC$_4$H$_9$ --; line 34, "3'-OCH$_5$" should read -- 3'-OCH$_3$ --; line 40, "6-C$_4$H$_3$" should read -- 6-C$_4$H$_9$ --; line 43, "5-1-C$_5$H$_{13}$" should read -- 5-i-C$_6$H$_{13}$ --; line 45, "3'-OC$_2$H$_5$  6" should read -- 3'-CH$_3$  5'-OC$_2$H$_5$  6 --;

Signed and Sealed this

Fourth Day of August 1981

[SEAL]

Attest:

GERALD J. MOSSINGHOFF

Attesting Officer  Commissioner of Patents and Trademarks